(12) United States Patent
Chen

(10) Patent No.: US 9,635,442 B1
(45) Date of Patent: Apr. 25, 2017

(54) CLOUD-BASED WATER QUALITY AND LEAK MONITORING SYSTEM

(71) Applicant: YEK HWA HARDWARE CO., LTD., Taipei (TW)

(72) Inventor: Tung-Hung Chen, New Taipei (TW)

(73) Assignee: YEK HWA HARDWARE CO., LTD., Taipei (TW)

( * ) Notice: Subject to any disclaimer, the term of this patent is extended or adjusted under 35 U.S.C. 154(b) by 0 days.

(21) Appl. No.: 15/075,200

(22) Filed: Mar. 21, 2016

(51) Int. Cl.
| G08C 19/22 | (2006.01) |
| H04Q 9/00 | (2006.01) |
| G01N 33/18 | (2006.01) |
| G01M 3/00 | (2006.01) |

(52) U.S. Cl.
CPC ............... *H04Q 9/00* (2013.01); *G01M 3/00* (2013.01); *G01N 33/18* (2013.01); *H04Q 2209/40* (2013.01)

(58) Field of Classification Search
None
See application file for complete search history.

(56) References Cited

U.S. PATENT DOCUMENTS

| 7,360,413 B2* | 4/2008 | Jeffries | G01M 3/2807 73/195 |
| 2007/0090059 A1* | 4/2007 | Plummer | C02F 1/008 210/743 |
| 2013/0145826 A1* | 6/2013 | Richarz | G01M 3/00 73/49.1 |
| 2013/0214936 A1* | 8/2013 | Schuberth | G01M 3/243 340/870.03 |
| 2015/0330863 A1* | 11/2015 | Dotan | F17D 5/06 702/51 |
| 2016/0025536 A1* | 1/2016 | Madsen | G01D 4/02 702/45 |

* cited by examiner

*Primary Examiner* — Adolf Dsouza
(74) *Attorney, Agent, or Firm* — Leong C. Lei

(57) ABSTRACT

The cloud-based water quality and leak monitoring system contains a server device on the Internet and a pipe device containing a main pipe and an auxiliary pipe connected to the main pipe in parallel. The pipe device further contains a pH detection element, a water pressure detection element, a turbidity detection element, and a flowmeter element. Various data from these elements is transmitted to the server device via WiFi or 4G wireless communications. The server device stores the various data so that a user is able to access, download, and view these data using a computer or a mobile device.

4 Claims, 8 Drawing Sheets

CLOUD-BASED WATER QUALITY AND LEAK MONITORING SYSTEM

BACKGROUND OF THE INVENTION (a) Technical Field of the Invention

The present invention is generally related to water monitoring, and more particular to a system capable of remotely monitoring household water quality and leakage.

(b) Description of the Prior Art

Tap water is indispensable in people's daily life. Before it is supplied to the households, tap water is appropriately filtered. However, impurities in the tap water cannot be completely removed. Especially when there is a typhoon, water turbidity increases significantly, thereby affecting the water quality. On the other hand, water leakage is often undetected, leading to a costly water bill and a significant waste of water resource. Currently there are techniques for installing monitoring devices in water pipes for detection of pH value, pressure, and flow of water, and for remotely accessing these data. However, there are no similar solutions for water leaking.

SUMMARY OF THE INVENTION

A major objective of the present invention is to provide a cloud-based water quality and leak monitoring system where water quality and leakage data can be accessed, downloaded, and viewed from Internet so as to take appropriate action in response to water quality change and leakage.

The cloud-based water quality and leak monitoring system contains a server device on the Internet and a pipe device configured between an outer pipe and an inner pipe of a household. The pipe device contains a main pipe and an auxiliary pipe connected to the main pipe in parallel. The pipe device further contains a pH detection element, a water pressure detection element, a turbidity detection element, and a flowmeter element, all configured on a circumferential wall of the main pipe. Various data from these elements is transmitted to the server device via WiFi or 4G wireless communications. The server device stores the various data so that a user is able to access, download, and view these data using a computer or a mobile device. Appropriate actions therefore can be conducted in response to water quality change and leakage.

The auxiliary pipe contains a channel of a smaller aperture and two water detection elements at the channel's two ends for detecting water flowing through the channel.

The water detection elements are supersonic detection elements.

The main pipe also contains a branch pipe having an inner end embedded into the main pipe and an outer end exposed outside the main pipe. The branch pipe contains a cap element sealing an outer end, an outlet element inside the branch pipe at the inner end. An actuation valve element is inside the branch pipe and contains a piston and a spring. The two ends of the spring are against the outer element and the cap element so that the actuation valve element is moveable to block or unblock the outlet element;

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

Figure 1:
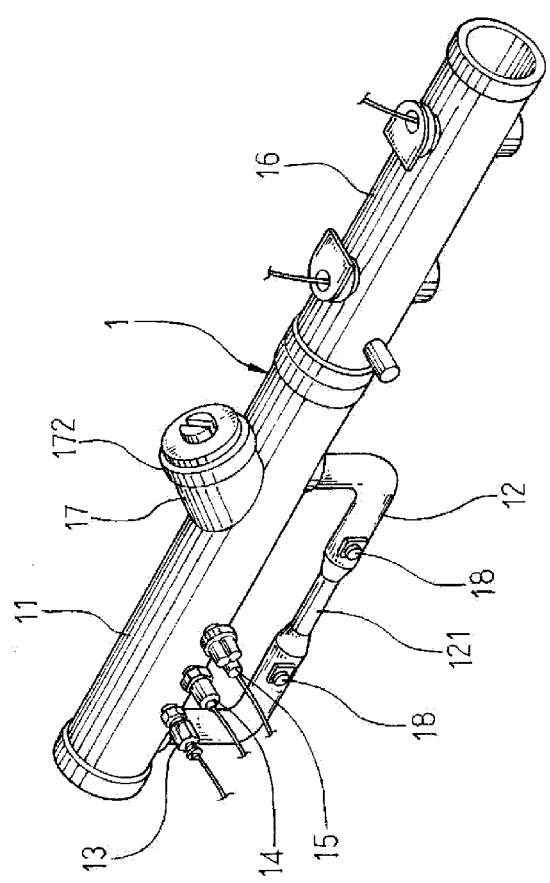
FIG. 1 is a perspective diagram showing a pipe device of the cloud-based water quality and leak monitoring system according to an embodiment of the present invention.
Figure 2:
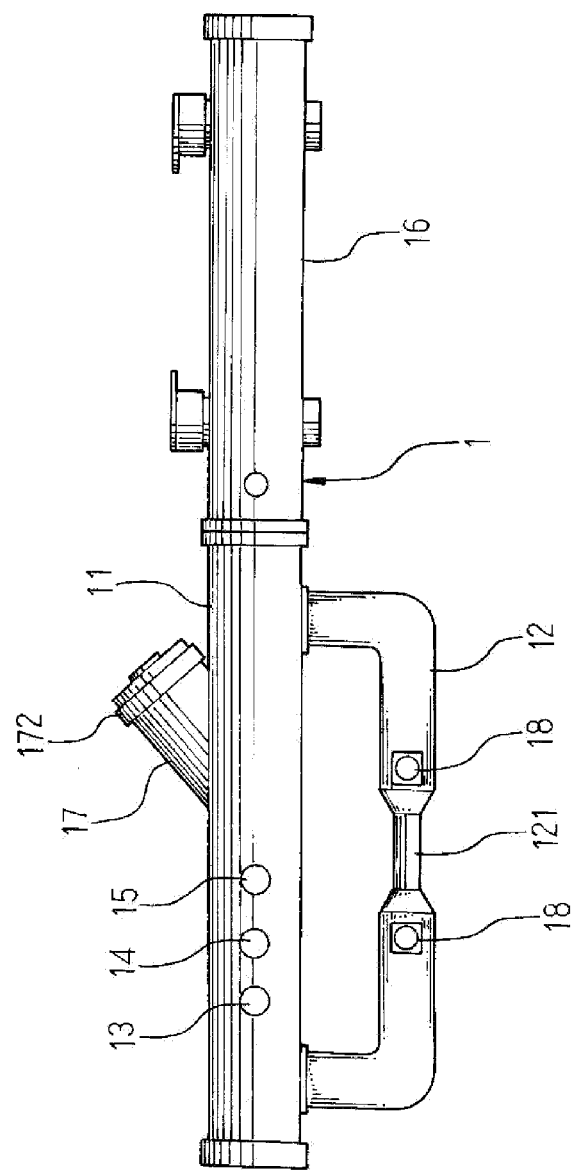
FIG. 2 is a side-view diagram showing the pipe device of FIG. 1.
Figure 3:
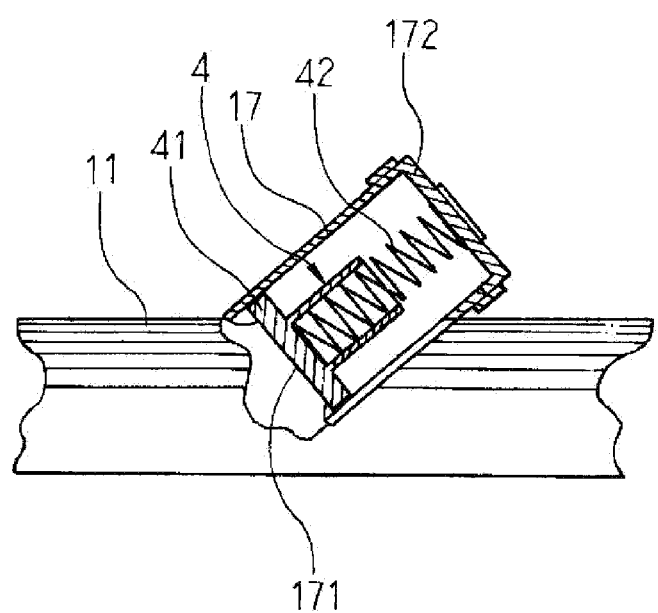
FIG. 3 is a schematic diagram showing an actuation valve element in the pipe device of FIG. 1.
Figure 4:
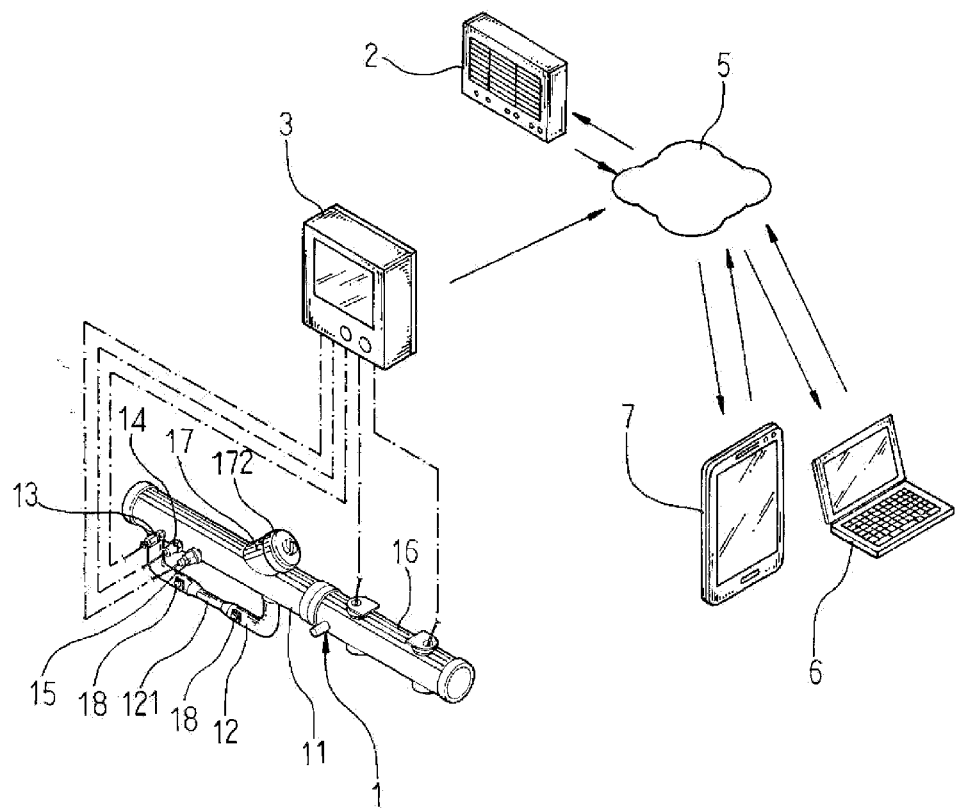
FIG. 4 is a schematic diagram showing an operation environment of the cloud-based water quality and leak monitoring system according to an embodiment of the present invention.

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

As shown in FIGS. 1 to 4, a cloud-based water quality and leak monitoring system according to an embodiment of the present invention contains a pipe device 1 and a server device 2 on the Internet. The pipe device 1 contains a main pipe 11 and an auxiliary pipe 12 connected to the main pipe 11's circumferential wall. The pipe device 1 further contains a pH detection element 13, a water pressure detection element 14, a turbidity detection element 15, and a flowmeter element 16. A branch pipe 17 has an inner end embedded into the main pipe 11. An outer end of the branch pipe 17 exposed outside the main pipe 11 is sealed by a cap element 172. Inside the branch pipe 17 and at the inner end, an outlet element 171 is configured to block at least a portion of the main pipe 11's cross section. The pH detection element 13, water pressure detection element 14, turbidity detection element 15, and flowmeter element 16 are configured on the circumferential wall of the main pipe 11, and are connected to a control device 3 with wireless communication capability through WiFi or 4G.

An actuation valve element 4 is configured in the branch pipe 17. The actuation valve element 4 contains a piston 41 and a spring 42 sequentially cascaded between the outlet element 171 and the cap element 172. The spring 42's two ends are against the piston 41 and the cap element 172, respectively. The piston 41 as such is moveable within the branch pipe 17 so as to seal an outlet (not shown) on the outlet element 171 or to move away from the outlet element 171.

The auxiliary pipe 12 contains a channel 121 of a smaller aperture and two water detection elements 18 at the channel 121's two ends for detecting water flowing through the channel 121. The water detection elements 18 are connected to the control device 3. In the present embodiment, the water detection element 18 is a supersonic element 18.

Figure 5:
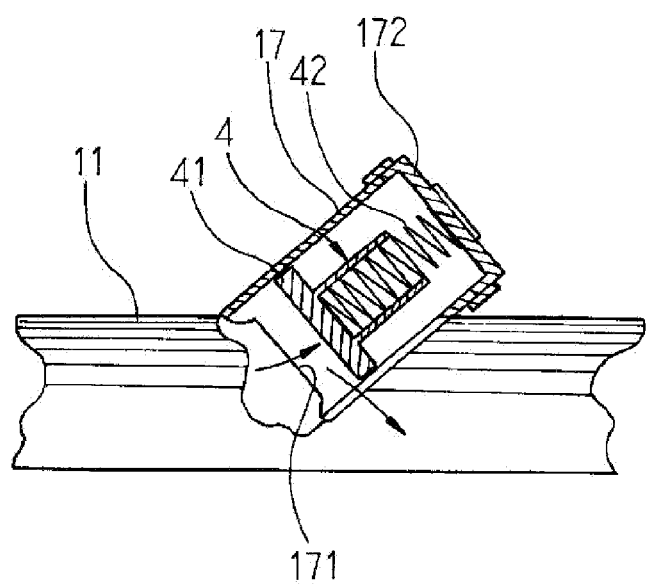
FIGS. 5 and 6 provide an operation scenario of the cloud-based water quality and leak monitoring systems of FIG. 4 in detecting water quality.
Figure 6:
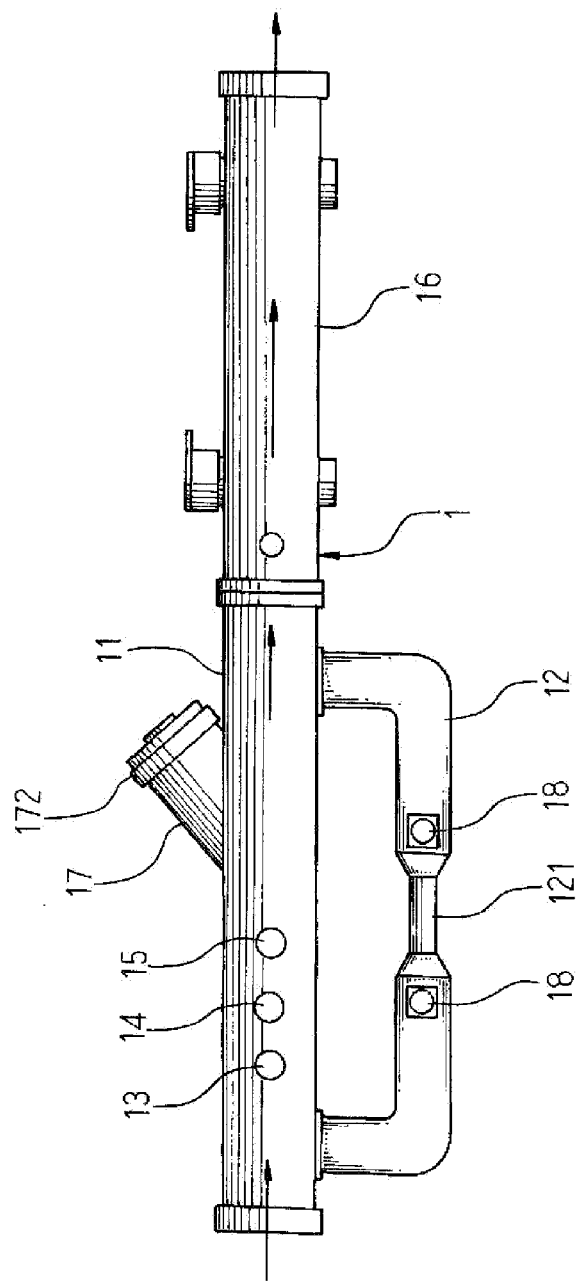

The cloud-based water quality and leak monitoring system operates as follows in monitoring water quality. The pipe device 1 is installed between an outer water pipe and an inner water pipe of a household (e.g., between the household's water meter and the inner pipe). As shown in FIGS. 5 and 6, when tap water is running normally (e.g., a faucet is turned on) and due to its greater volume, it will push the actuation valve element 4's piston 41 away from the outlet element 171 of the branch pipe 17, and it will continue to flow through the outlet element 171 and the main pipe 11 to achieve normal water provision. The pH detection element 13, water pressure detection element 14, turbidity detection element 15, and flowmeter element 16 detect the pH value, water pressure, turbidity, and flow volume, and transmit the various data to the server device 2 on the Internet 5 through the control device 3 using WiFi or 4G. The server device 2 stores the various data so that a user is able to access, download, and view these data using a computer 6 or a mobile device 7 (e.g., smart phone) at all times, and the user is therefore able to take appropriate action. For example, after a typhoon, the turbidity of water increases rapidly, the user is able to learn this situation through the present embodiment, and prepares water from separate and cleaner sources. After the water turbidity drops, the user is also able to learn this through the present embodiment and resumes to use tap water.

Figure 7:
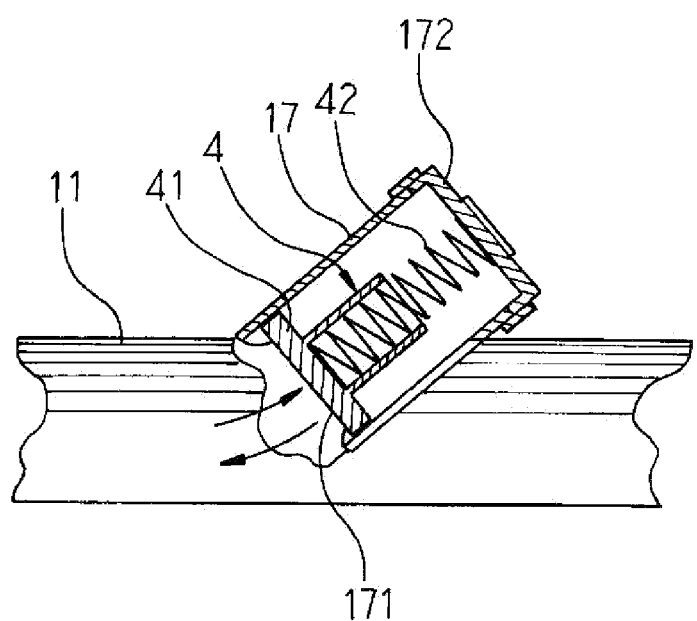
FIGS. 7 and 8 provide an operation scenario of the cloud-based water quality and leak monitoring systems of FIG. 4 in detecting water leakage.
Figure 8:
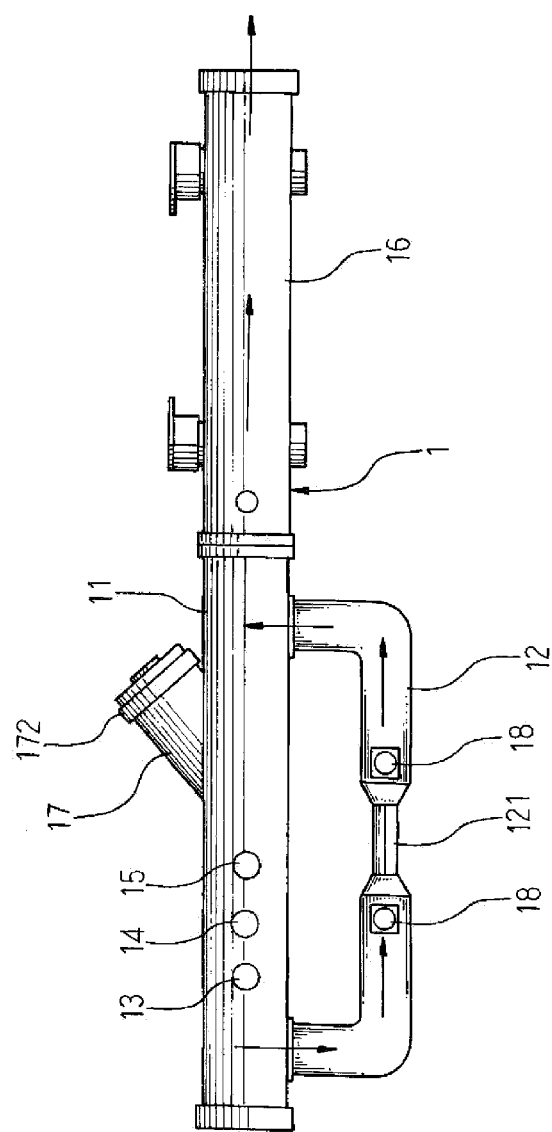

The cloud-based water quality and leak monitoring system operates as follows in detecting water leaking. As shown in FIGS. 7 and 8, when tap water is stopped normally (e.g., all faucets are turned off) and due to its smaller volume, the spring 42's pressure prevents the water from pushing the actuation valve element 4's piston 41 away from the outlet element 171 of the branch pipe 17. The piston 41 blocks the outlet element 171 and at least a portion of the water is not able to flow through the main pipe 11. If there is water leakage, a small volume of water will flow through the auxiliary pipe 12 and its channel 121. The water detection elements 18 will detect this small volume of water and transmit the data to the server device 2 on the Internet 5 through the control device 3 using WiFi or 4G. The server device 2 stores the data so that the user is able to access, download, and view the data using computer 6 or mobile device 7. The user is therefore able to take appropriate action to prevent waste of water resource.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A cloud-based water quality and leak monitoring system comprising a server device on the Internet and a pipe device configured between an outer pipe and an inner pipe of a household, wherein the pipe device comprises:
    a main pipe,
    a branch pipe having an inner end embedded into the main pipe and an outer end exposed outside the main pipe,
    the branch pipe comprises a cap element sealing the outer end, an outlet element inside the branch pipe at the inner end, and an actuation valve element inside the branch pipe between the outer element and the cap element moveably blocking the outlet element;
    an auxiliary pipe connected to a circumferential wall of the main pipe,
    the auxiliary pipe comprises a channel of a smaller aperture and two water detection elements at the channel's two ends for detecting water flowing through the channel,
    a control device capable of wireless communications through WiFi or 4G; and
    the water detection elements are connected to the control device;
    for a small volume of water resulted from leakage, a spring's pressure prevents the small volume of water from pushing the actuation valve element's piston away from the outlet element of the branch pipe;
    the water detection elements detect the small volume of water when it flows through the auxiliary pipe and the channel, and transmit data to the server device through the control device; and
    the server device stores the data so that a user is able to access, download, and view the data using a computer or a mobile device.

2. The cloud-based water quality and leak monitoring system according to claim 1, wherein the actuation valve element comprises a piston and a spring sequentially cascaded between the outlet element and the cap element; the spring's two ends are against the piston and the cap element, respectively; the piston as such is moveable within the branch pipe so as to seal the outlet element or to move away from the outlet element.

3. The cloud-based water quality and leak monitoring system according to claim 1, wherein the water detection elements are supersonic detection elements.

4. The cloud-based water quality and leak monitoring system according to claim 1, wherein the pipe device further comprises a pH detection element, a water pressure detection element, a turbidity detection element, and a flowmeter element, all configured on the circumferential wall of the main pipe and connected to the control device; when water is running normally, water pushes the actuation valve element's piston away from the outlet element of the branch pipe, and continues to flow through the outlet element and the main pipe while the pH detection element, water pressure detection element, turbidity detection element, and flowmeter element detect the pH value, water pressure, turbidity, and flow volume, and transmit various data to the server device through the control device; the server device stores the various data so that a user is able to access, download, and view these data using a computer or a mobile device.

* * * * *